US00PP21206P3

(12) United States Plant Patent
Merritt

(10) Patent No.: US PP21,206 P3
(45) Date of Patent: Aug. 17, 2010

(54) LILY PLANT NAMED 'BJM 006'
(50) Latin Name: *Lilium species×L. longiflorum*
Varietal Denomination: BJM 006

(75) Inventor: Richard H. Merritt, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 12/317,962

(22) Filed: Dec. 30, 2008

(65) Prior Publication Data

US 2010/0170020 P1 Jul. 1, 2010

(51) Int. Cl.
*A01H 5/00* (2006.01)

(52) U.S. Cl. ..... Plt./313
(58) Field of Classification Search ..... Plt./313
See application file for complete search history.

*Primary Examiner*—Annette H Para
(74) *Attorney, Agent, or Firm*—Klarquist Sparkman, LLP

(57) ABSTRACT

A new and distinct lily plant substantially as shown and described, characterized by 1) stem thickness supported by flower crown (8 to 10 mm in diameter); (2) straight stems with even leaf distribution from bottom to top (more than 50 leaves per plant); (3) flower crown compact (around 36 cm); and flat with pericel lengths variable in length (1 to 8 cm); (4) flower sizes large (9-16 cm long 20-25 cm wide at open stage); (5) continuous blooms for two to four weeks; (6) coloration of leaves uniform from bottom to top; (7) height of plant around 40 cm; and (8) orange flowers.

1 Drawing Sheet

Latin name of the genus and species of the plant claimed: *Lilium* species×*L. longiflorum.*

Variety denomination: 'BJM 006'.

FIELD

The present invention comprises a new and distinct cultivar of *Lilium* named 'BJM 006' characterized by very large orange (flame) compact flower crowns on strong stems with rich green foliage. This cultivar in the garden will produce a garden/specimen plant with 5 or more blooms.

SUMMARY

A new and distinct cultivar of *Lilium* named 'BJM 006' substantially as herein shown and described in FIG. 1. The parentage is *Lilium* species '*Henryi*' (unpatented)×a *L. longiflorum* hybrid cv whose parentage is not known. The cv was developed as part of a breeding program in New Brunswick, N.J.

The new variety is characterized by numerous very large orange compact flowers on short straight strong stems with rich green plentiful foliage. The following traits have been repeatedly observed in asexually propagated progeny and are determined to be the basic characteristics of this invention which in combination distinguish this lily as a new and distinct cultivar: (1) stem thickness supported by flower crown (8 to 10 mm in diameter); (2) straight stems with even leaf distribution from bottom to top (more than 50 leaves per plant); (3) flower crown compact (around 36 cm); and flat with pericel lengths variable in length (1 to 8 cm); (4) flower sizes large (9-16 cm long 20-25 cm wide at open stage); (5) continuous blooms for two to four weeks; (6) coloration of leaves uniform from bottom to top; (7) height of plant around 40 cm; and (8) orange flowers. To the inventor's knowledge, there are no other cultivars of lily of this size of plant or in terms of the superior plant and flower quality in the market.

'BJM 006' has been asexually reproduced by tissue culture in New Brunswick, N.J. No evidence of off-types of 'BJM 006' have been observed or reported to us. Thus, it is concluded that 'BJM 006' is stable and reproduces true to type in successive generations of asexual reproduction.

The following detailed description concerns the variety 'BJM 006'. The description herein provided are from plants grown from cooled 10 g bulbs placed in a 60° F. N/70°F. D greenhouse for 4 months at which time they bloomed. Progeny of the original plant have been observed growing in cultivated areas in New Brunswick, N.J. Certain characteristics of this variety, such as growth and color, may change with changing environmental conditions (such as light, temperature, moisture, nutrient availability, soil or other factors). Color descriptions and other terminology are used in accordance with their horticultural descriptions, unless the context clearly indicates otherwise. Color designations are used with reference to The Royal Horticultural Society (R.H.S.) Colour Chart and Munsell Color Charts for Plant Tissues (Munsell Chart 10R Value 6 Chrome 10).

Figure 1:
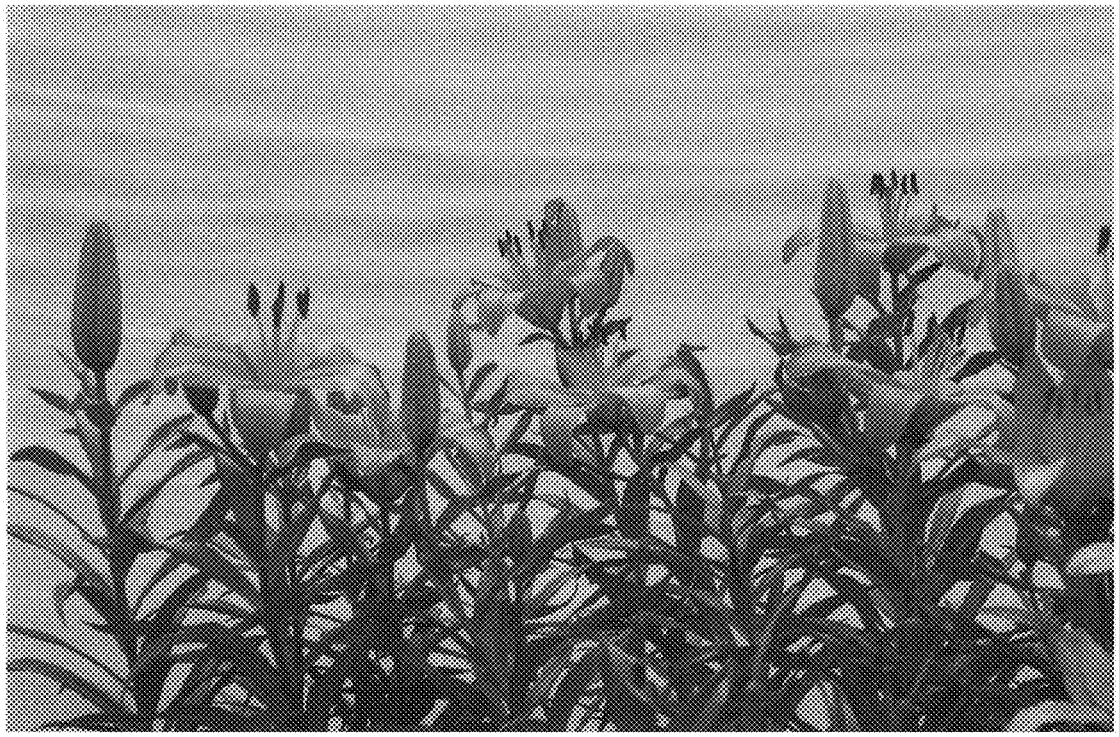
FIG. 1 is a photograph showing the new cultivar.

The colors of an illustration of this type may vary with lighting and other conditions and, therefore, color characteristics of this new variety should be determined with reference to the observations described herein, rather than from this illustration alone.

BOTANICAL DESCRIPTION

Relating to the plant:

*Origin.*—New Brunswick, N.J.

*Parentage.*—*Lilium* species *Henryi*×*L. longiflorum* hybrid (4-8×7-4).

*Seed parent.*—*Lilium* species *'Henryi'*.

*Pollen parent.*—*L. longiflorum* hybrid (4-8×7-4).
*Commercial classification.*—Bedding, specimen plant.
*Classification.*—Division 5, according to the Horticultural Classification of Lilies by The Royal Horticultural Society of London.
*Height.*—Approximately 40 cm from the top of the soil to the top of the flowers from bulbs of 8 cm in circumference.
*Stem color.*—Green — Munsell 5 GY, V6/C6.
*Stem diameter.*—8 mm to 10 mm.
*Growth habit.*—Upright, strict.
*Foliage.*—Predominantly cauline.
*Leaf arrangement.*—Alternate.
*Leaf size.*—Approximately 16 cm long×1.5 cm to 2.0 cm wide.
*Leaf shape.*—Linear-lanceolate.
*Texture.*—Shining and glabrous.
*Color.*—Light green — Munsell 5GY V4/C4.
*Size.*—Variable, ranging to approximately 15 cm in circumference as used commercially.
*Color.*—White.

The bud:
*Size.*—10 cm long and 2 cm to 2.5 cm wide just prior to opening.
*Shape.*—Ellipsoidal, sulcate.
*Rate of opening.*—Dependent on temperature.
*Color.*—Munsell Yellow-Red 5 YR 5V/10C.

The flower:
*Blooming habit.*—Terminal inflorescence with 3 or more companion upright flowers.
*Days to bloom.*—120 days.
*Inflorescence size.*—Approximately 13 cm high and 12 cm wide when there are 4 flowers present.
*Flower size.*—Large.
*Diameter.*—Approximately 13 cm.
*Depth.*—Approximately 12 cm.
*Borne.*—In an umbel or modified raceme of 3-5 flowers from bulbs 15 cm in circumference.
*Shape.*—Partially open.
*Tepals.*—Orange reflex.
*Tepal number.*—6.
*Flower color.*—210 B-7 Flame (BEHR premium).
*Arrangement.*—Alternate.
*Tepal shape.*—Ovate.
*Texture.*—Shining and glabrous.
*Nectary.*—Description: obscure.
*Projections.*—Absent.
*Spots.*—Absent.
*Blush.*—Absent.
*Fragrance.*—Absent.
*Pedicel.*—All terminal, dark green, glabrous.
*Length.*—Approximately 2-6 cm.
*Orientation.*—Ascending upwardly at an angle of 75° from the horizontal.

The reproductive organs:
*Stamens.*—Slightly exserted.
*Number.*—6.
*Anthers before dehiscence.*—Approximately 1 cm. Color: Munsell 10R, V4/C10.
*Filaments.*—Length: 4 cm Color: Munsell 210 B-7 Flame.
*Pollen.*—Color: Munsell 1OR 3V/4C.
*Pistil.*—1 in number.
*Style.*—Length: 4 cm Color: Munsell 5Y 7V/10C.
*Stigma.*—Color: Munsell 5Y 7V/10C.

The fruit:
*Fertility.*—Absent.

BJM 006 is different from the parents as indicated below: The pistillate parent *L. Henryi* is a tall 4 foot plant with orange pendant flowers with brown spots, raised papillae and green centers. The staminate parent is a very short white flowered hybrid from the NJAES Lily Breeding Program. 'BJM 006' is ¼ the height of *L. Henryi* and about ¼ taller than the *L. longiflorum* plant. 'BJM 006' has a flower form very similar to the *L. longiflorum* parent, but pigmented, not white. The new variety is very different in form from *L. Henryi* and has no brown spots on the flower.

I claim:

1. A new and distinct lily plant as herein illustrated and described.

* * * * *